United States Patent [19]
Deoms et al.

[11] Patent Number: 5,500,187
[45] Date of Patent: Mar. 19, 1996

[54] DISPOSABLE OPTICAL AGGLUTINATION ASSAY DEVICE AND METHOD FOR USE

[75] Inventors: James H. Deoms, Glenarm; Daryl S. Mileaf; Kevin E. LaCour, both of Jessup; Noe E. Rodriguez, II, Severna Park; Joseph M. Leginus, Silver Spring; Scott D. Johnson, Elkridge; Richard C. Kapraun, Baltimore; Richard M. Young, Millersville, all of Md.

[73] Assignee: Westinghouse Electric Corporation, Pittsburgh, Pa.

[21] Appl. No.: 986,816

[22] Filed: Dec. 8, 1992

[51] Int. Cl.⁶ .......................... G01N 33/558; G01N 33/94
[52] U.S. Cl. .......................... 422/58; 422/61; 422/73; 435/287.1; 435/810; 435/287.2; 435/288.7; 436/164; 436/165; 436/514; 436/531; 436/534; 436/536; 436/538; 436/541; 436/805; 436/807; 436/815
[58] Field of Search .............................. 435/33, 287, 291, 435/294, 295, 810; 436/517, 501, 514, 531, 534, 536, 538, 541, 164, 165, 805, 807, 815; 422/73, 58, 60, 61

[56] References Cited

U.S. PATENT DOCUMENTS

| | | | |
|---|---|---|---|
| 4,596,695 | 6/1986 | Cottingham | 422/58 |
| 4,673,657 | 6/1987 | Christian | 436/501 |
| 4,756,884 | 7/1988 | Hillman et al. | 422/73 |
| 4,775,515 | 10/1988 | Cottingham | 422/73 |
| 4,918,025 | 4/1990 | Grenner | 422/58 |
| 5,019,351 | 5/1991 | Schulz | 422/99 |
| 5,039,617 | 8/1991 | McDonald et al. | 436/69 |
| 5,154,888 | 10/1992 | Zander et al. | 422/58 |
| 5,254,479 | 10/1993 | Chemelli | 422/58 |

*Primary Examiner*—Toni R. Scheiner
*Assistant Examiner*—Christopher L. Chin

[57] ABSTRACT

An assay device for detecting the presence of analytes in an unknown sample including a reaction system wherein storage reservoirs containing reagent are fluidly connected to a track containing the sample. An actuation mechanism forces the reagent from the reservoirs and into the track where it mixes the reagents together and then with the sample at a first flow rate. The mechanism then reduces the force on the reagent to allow a second flow rate less then the first flow rate to force the reagent and sample mixture through the track so that reaction can occur, whereby a determination as to whether the target analyte was present may be made.

20 Claims, 7 Drawing Sheets

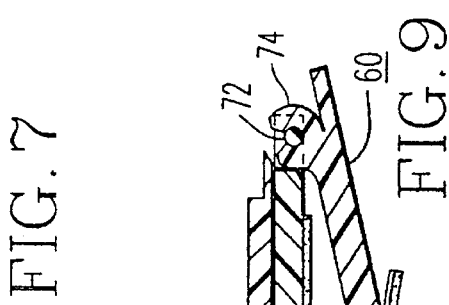
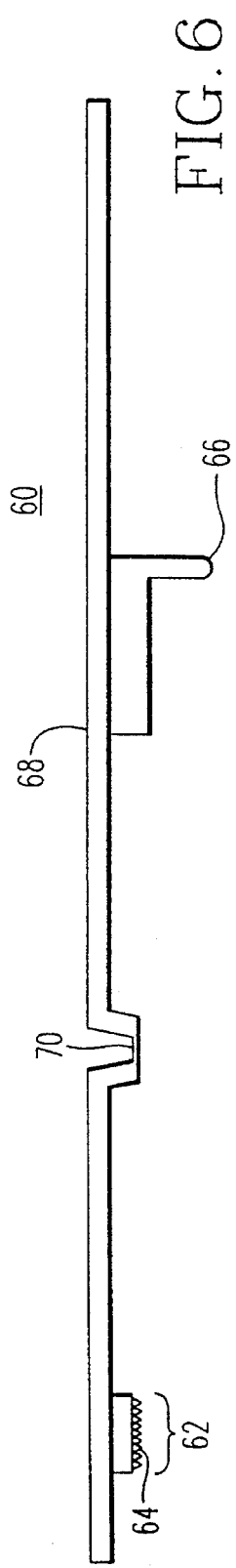
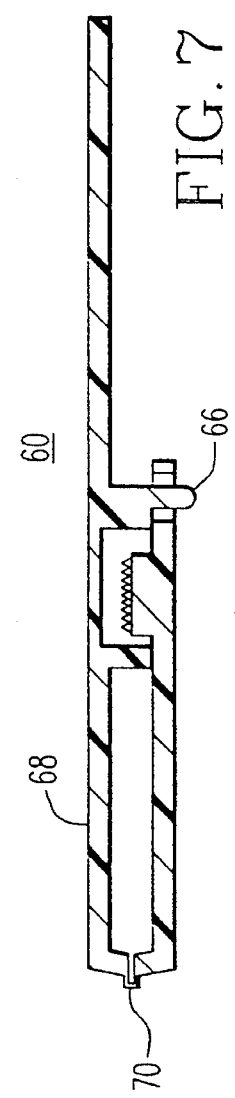
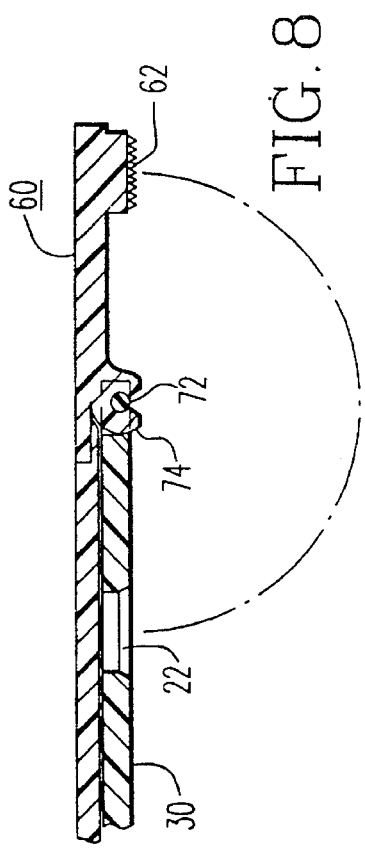

DISPOSABLE OPTICAL AGGLUTINATION ASSAY DEVICE AND METHOD FOR USE

BACKGROUND OF THE INVENTION

1. Field of the Invention

The present invention relates to devices for detecting the presence of analytes. In particular, the invention relates to such devices whereby disposable assays may be quickly and efficiently conducted in the field. More particularly, the invention relates to an assay device which may be selectively controlled by an actuation device of predetermined speed and/or pressure.

2. The Prior Art

There is a present and continuing need to detect a wide variety of analytes with high specificity and high sensitivity in many applications. A technique that is well known in the art uses antibody/antigen (antibody generator) reactions to determine a target analyte. One common use of the antibody/antigen pair is in the construction of a reaction environment in which microscopic particles to which antibody or antigens have been chemically attached are made to agglutinate or are inhibited from agglutinating in the presence of the mating antibody/antigen and the target analyte.

When an agglutination reaction occurs, the microscopic particles chemically bind to each other with the antibody/antigen molecules serving as very specific chemical binding agents, forming much larger aggregates of particles which can grow in size to become visible to the naked eye. The progress of the reaction may be monitored and resulting data analyzed to provide quantitative and qualitative results on target analyte concentration.

A specific agglutination reaction is latex agglutination. Latex agglutination tests are available which detect small qualities of antigen molecules. Agglutination reactions usually involve the aggregation of latex particles which bear on the surface antigenic molecules. Aggregation (agglutination) occurs when antibody molecules specifically corresponding to the antigen (e.g. cocaine) are introduced into the solution of the carrier particles. Antibodies can be visualized as having a "Y" shape where both arms of the "Y" can attach antigen. Mixing antigen-coated latex particles and antibody causes these components to interact and combine. As more antibodies and particles become involved, many cross-linkages are formed and the particles group together as visible clusters. However, when free, unbounded antigen is introduced from an external sample, for instance, agglutination does not occur. The free antigen caps the antibody binding sites and inhibits the agglutination.

Devices are known in the art which can detect various analytes. However, these devices require numerous steps that are not conducive to being used in the field environment, with minimal training, in a simple sequence, to provide consistent results. An assay device designed for ease of use by the person performing the test would be desirable.

Devices are known which require a user to add the required reagents and preform a crude stirring or mixing operation which is subject to not being repeatable in the field. Carrying the required reagents, measuring the exact proportions, and mixing the reagents in the assay device are steps which are not conducive to ease of use with minimal training. It would be desirable to have an assay device which contained the premeasured reagents needed to perform a specific test to determine if a suspect substance contained a target analyte. Additionally, it would be desirable to have an assay device which was designed to adequately mix the reagents upon being actuated before being introduced to the sample or suspect substance for further mixing.

Known devices require the assay device to be held still or horizontal while the reagent and sample mixture flow through the assay device to get an agglutination result. Some devices require close tolerances in manufacturing to obtain capillary flow. Other known devices require the white room environment of a laboratory. It would be desirable for operators in the field to have an assay device that could be used by simply placing a sample to be tested into the device and triggering an actuator which would quickly and repeatedly carry out the test without room for operator error. It would also be desirable to have a device resistant to an abusive environment of rough handling and jostling around even while the test was being conducted.

This application is related to U.S. Pat. No. 5,290,517 entitled "Optical Agglutination Assay Device", filed Apr. 4, 1990 and assigned to the same assignee as the present application. and merely incorporated by reference. While the applications disclose different design configurations for the assay device, both may be utilized with an optical transmitting and receiving unit for measuring the intensity of light reflected from or transmitted through an optical viewing area in a track as a measure of the occurrence of agglutination in the reaction system.

A simple, inexpensive, portable, disposable, user friendly device for the collection and subsequent reaction of an unknown analyte with the requisite reagents is disclosed in this application.

SUMMARY OF THE INVENTION

Accordingly, it is an object of the present invention to provide an apparatus for the detection and measurement of an analyte in a sample or on a surface.

It is another object of the present invention to provide an apparatus for receiving a sample, all necessary reagents and the requisite tracks for controlling the mixing of the reagents and further mixing of the reagents with the sample in a low cost disposable unit that provides for a simple sample collection and user initiated reaction.

A further object of the present invention is to provide a unique collection apparatus which will mate with a reusable photometric reaction cell reading device and provide a qualitative or quantitative determination of the analyte concentration in the test sample.

It is an advantage of the present invention that the reagents required for testing a specific analyte are contained in the device and ready for mixing with a suspect sample. The user simply need introduce the suspect sample to the assay device, then actuate the device to cause the reagents and sample to mix, whereby results can then be analyzed.

Additional objects and advantages of the invention will be set forth in the description which follows, and in part will be apparent from the description, or may be learned by practice of the invention. The objects and advantages of the invention may be realized and obtained by means of the methods, instrumentalities and combinations particularly pointed out in the appended claims.

To achieve the foregoing objects, and in accordance with the purposes of the invention as embodied and broadly described herein, an appropriately designed assay device is provided in which an antibody/antigen agglutination reaction may be initiated and optically analyzed. The optical analysis can be either by the naked eye or a signal generated by a photodetector to determine either qualitative or quantitative information about the concentration of specific analytes which are present in the reaction mixture undergoing agglutination. The techniques used in the antibody/antigen interaction are specific and sensitive. Therefore, this approach becomes a generic one for the detection of analytes for which an antibody/antigen pair can be made. Furthermore, because of the unique design of the assay device the apparatus can be easily configured into a low cost disposable reaction assay device collector assembly for use in a hand-held portable detection unit.

In accordance with the present invention, the assay device for analyzing a sample of unknown substance by mixing a reagent with the sample comprises a housing having at least one storage reservoir containing reagent. The housing has an entry port for receiving the sample suspected of containing a target analyte into the housing. At least one track for controlling the reagent flow rate and mixing characteristics fluidly connects the reagent with the entry port for mixing the reagents with the sample. The assay device may further contain a track fluidly connected to the entry port for reacting the reagent and sample mixture. The reacting track may have a viewing area for analyzing the results of the reagent and sample mixture.

One embodiment of the assay device in accordance with the present invention includes a card having a first and opposing surface with an entry port extending from the first surface to the opposing surface. A flexible member contacts the opposing surface of the card to define at least one storage reservoir. At least one track for controlling the reagent flow rate and mixing characteristics is defined by the flexible member and the card through which reagent can be transferred between the storage reservoir and the entry port. The flexible member is deformable to force reagent between the storage reservoir and the entry port. The device further includes a track which is fluidly connected to the entry port for reacting the reagent and sample mixture. The reacting track may have an optical viewing area for viewing the results of mixing the reagent and the sample for determining the sample substance identity. A delivery means for conveying a sample suspected of containing a target analyte into the entry port may be included. The device may additionally include mixing and delivery means for transferring the reagent at a first flow rate to the sample in the entry port for further mixing. The reagent and sample mixture is then forced through the reacting track at a second flow rate less than the first flow rate so that reaction can occur.

BRIEF DESCRIPTION OF THE DRAWINGS

The accompanying drawings, which are incorporated in and constitute a part of the specification, illustrate a presently preferred embodiment of the invention which, taken with the general description given above and the detailed description of the preferred embodiment given below, serve to explain the principles of the invention. In the drawings:

FIG. 6 is a side view of a preferred swab with protective closure in an opened position;

FIG. 7 is a cross-sectional side view of the preferred swab shown in FIG. 6 in a closed position;

FIG. 8 is a cross-sectional side view of a preferred hinged swab in the opened position;

FIG. 9 is a cross-sectional side view of the preferred hinged swab shown in FIG. 8 engaged with a swab retainer strip;

DETAILED DESCRIPTION OF THE PREFERRED EMBODIMENT

Figure 1:
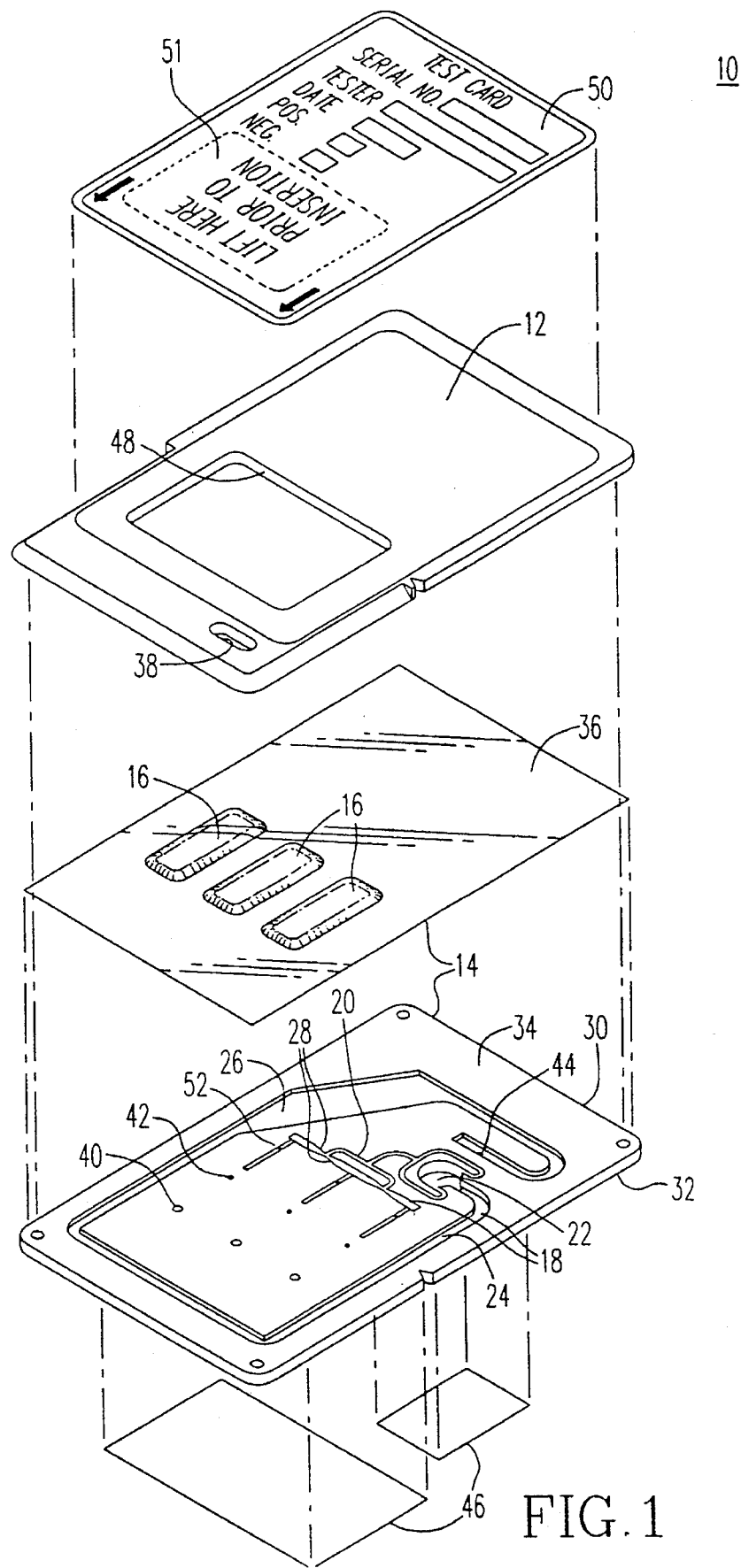
FIG. 1 is an exploded view of a preferred assay device which embodies the concepts and principles of the present invention.
Figure 2:
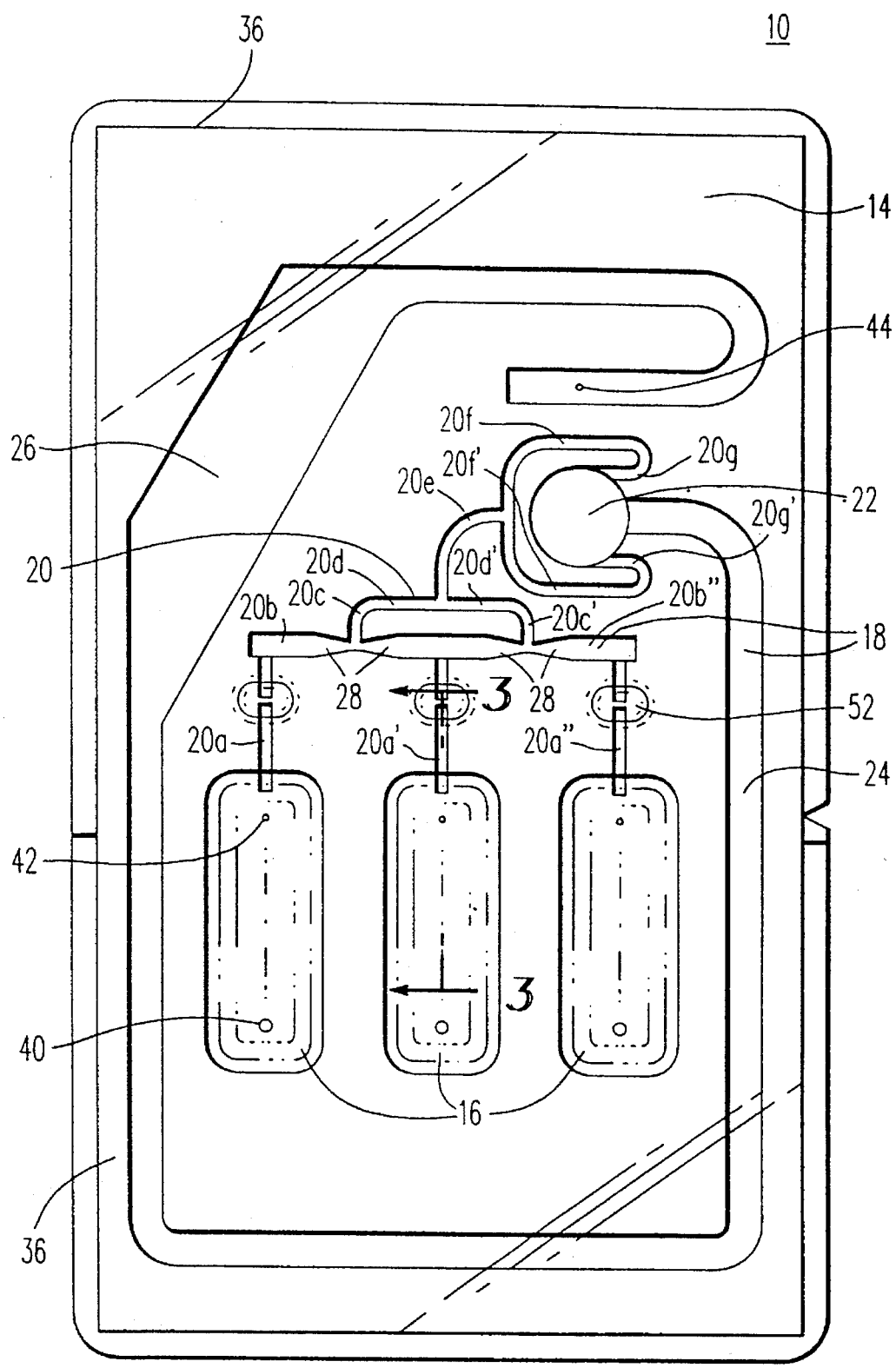
FIG. 2 is a top view of the preferred assay device shown in FIG. 1 without a cover member.

A preferred embodiment of the assay device 10 in accordance with the present invention is illustrated in FIGS. 1 and 2. FIG. 1 shows an exploded view of the device 10, while a top view of the device 10 without a cover member 12 is illustrated in FIG. 2. Device 10 includes a housing 14, storage reservoirs 16 containing reagent, and track 18. The track 18 which is fluidly connected to the storage reservoirs 16 serves different purposes at various stages of the track 18. The track 18 can be viewed as having the following portions: controlling track 20 fluidly connected to the storage reservoirs 16 for controlling the reagent flow rate and mixing characteristics; receiving track or an entry port 22 fluidly connected to the controlling track 20 for receiving a sample suspected of containing a target analyte into the housing 14; reacting track 24 fluidly connected to the entry port 22 for reacting the reagent and sample mixture; and an accumulator track or accumulator reservoir 26 in the reacting track 24 for retaining excess reagent and sample mixture.

The number of storage reservoirs 16 is dependent upon the reagents required for detecting a particular target analyte. At least one storage reservoir 16 is needed to contain a reagent or mixture of reagents. If a particular set of reagents can be premixed instead of being mixed just prior to actuation with the sample then one storage reservoir may be all that is required.

The controlling track 20 may have any number of fluidly connected paths to the reservoir 16 for dividing, agitating and mixing the reagents. By way of example and as best illustrated in FIG. 2, the controlling track 20 includes a first portion 20a, 20a' and 20a", each of a predetermined cross-sectional area, in fluid communication with a respective one of the reservoirs 16. Each portion 20a, 20a' and 20a" discharges into a respective second portion 20b, 20b' and 20b", each of a cross-sectional area greater than that of the first portion to which it is connected.

A third portion of controlling track 20 is formed by branches 20c and 20c' which then joins with respective fourth portions 20d and 20d'. These fourth portions 20d and 20d' both discharge into a fifth portion 20e of controlling track 20. Fluid in fifth portion 20e is divided in sixth portions 20f and 20f' which bend around to form final and seventh portions 20g and 20g' positioned to discharge fluid tangentially into the entry port 22. Under circumstances where only one storage reservoir 16 is required, the controlling track 20 may still provide a means for mixing the reagent prior to introducing the reagent to the sample, thereby eliminating any need for shaking the reagent prior to actuation. A nozzle or set of nozzles 28 for assisting in mixing the reagents through changing flow rates and turbulently mixing the reagents together are be included in portions 20b, 20b' and 20b" of controlling track 20. Additionally, the nozzles 28 can be used to control the flow rate of the reagent to insure that the reagent flow rate is sufficient to mix the reagent and sample together.

The nozzles 28 serve as a means for mixing the reagents by having the reagents collide at an accelerated speed. In a preferred embodiment the nozzles 28 are molded into the portions 20b, 20b' and 20b" of controlling track 20 to form mixing points. Between nozzles 28, the cross-section of the controlling track 20 may be increased in order to increase the hydraulic diameter of the controlling track 20, which in turn lowers the frictional head loss in the controlling track 20. Lower head loss will allow more actuation energy used to force reagent from the reservoirs 16 to be used to increase fluid velocity instead of frictional losses. The nozzles 28 may be created by stepping the controlling track 20 up or down in cross-section. However, the preferred method is ramping the controlling track 20 with smooth, straight or curved tapers. Not only does this method lower the frictional head losses, but results in fewer air bubbles entering the system. A preferred embodiment of controlling track 20 has the reagent flow turn ninety degrees into portions 20c and 20c' after a head-on collision of the reagents. After the reagents collide and are turned to continue further down the controlling track 20, the controlling track 20 is slightly larger in cross-sectional area so that no unnecessary flow resistance is created. The number of nozzles 28 used in a particular assay device 10 may vary with the specific reagent flow rate and mixing characteristic requirements.

A preferred embodiment of the assay device 10 for detecting a target analyte can be best understood by the exploded view of the device 10 illustrated in FIG. 1. The optical agglutination assay device 10 includes a card 30 having a first surface 32 and an opposing surface 34 with an entry port 22 extending from the first surface 32 to the opposing surface 34. A flexible member 36 contacts the opposing surface 34 of the card 30 forming at least one reservoir 16 containing reagent and covering the track 18, which is molded into the opposing side 34 of the card 30. At least one controlling track 20 for controlling the reagent flow rate and mixing characteristics is defined by the flexible member 36 and the card 30 through which the reagent can be transferred between the reservoir 16 and the entry port 22. The flexible member 36 is deformable to allow the reagent to be forced between the reservoir 16 and the entry port 22. The reacting track 24 is fluidly connected to the entry port 22 for reacting the reagent and sample mixture. The reacting track 24 has an optical viewing area 38 for viewing the results of mixing the reagents and the sample to determine the sample substance identity.

In a preferred embodiment the flexible member 36 covers the entry port 22 on the opposing surface 34 of the card 30 as well as the track 18 which is preferably recessed into the opposing surface 34 of the card 30. Additionally, in an alternative embodiment the card 30 and flexible member 36 may be composed of a single piece housing 14 having a flexible top surface.

Preferably the card 30 is made of molded plastic, such as polystyrene. The track 18 through which the reagent flows is molded directly into the card 30. The reservoirs 16 are vacuum-formed into a sheet of polyester film, while the film is being heat-sealed over the side of the card 30 in which the track 18 is molded. This straight-forward process takes less than a minute to complete.

Fill holes 40 are used for filling the reagent storage reservoirs 16 with reagent. Vent holes 42 allow excess air to be displaced from the system during the filling process. Another ventilation hole 44 is shown at the opposite end of track 18 from where the track 18 connects to the reservoirs 16. The purpose of this ventilation hole 44 is to permit any excess air to escape from the track 18 when the reagents are forced from the reservoirs 16. Tape 46 covers the holes 40, 42, and 44 respectively. The tape 46 covering ventilation hole 44 is preferably removed prior to conducting a test with the device 10.

To prevent reaction product from leaking out of the ventilation hole 44 the accumulator reservoir 26 is molded into the reacting track 24. This cavity has the capacity to hold all of the reagent volume in the reservoirs 16.

In a preferred embodiment a cover member 12 made of molded plastic is used to sandwich the flexible member 36 between the card 30 and the cover member 12 to protect the system from being ruptured. Additionally, the cover member 12 has an opening 48 to allow access to the reservoirs 16 for actuating the device 10 by applying pressure to the reservoirs 16 to force the reagents through the track 18. The reservoirs 16, which are not as high as the cover member 12 is thick, protrudes into the opening 48. The optical viewing area 38 is in the cover member 12 to enable the reaction of the reagents and sample or reaction product as it passes through the reacting track 24 to be observed to determine the results of the test. The cover member 12 is ultrasonically welded to the card 30; although the cover member 12 could also be attached with adhesive or doubled-sided tape by way of example.

A removable label 50 covers opening 48 in the cover member 12 to further protect the reservoirs 16 from accidental actuation. Additionally, the label 50 provides information identifying the target analyte the device 10 is designed for testing. A portion 51 the label 50 covering the reservoirs 16 and viewing area 38 is simply removed after the sample has been introduced to the device 10 and the user desires to carry out the test. The label 50 is made of stiff paper and coated with a high tack/low tack adhesive so that it can be easily and cleanly removed by the user at the appropriate time.

Figure 3:
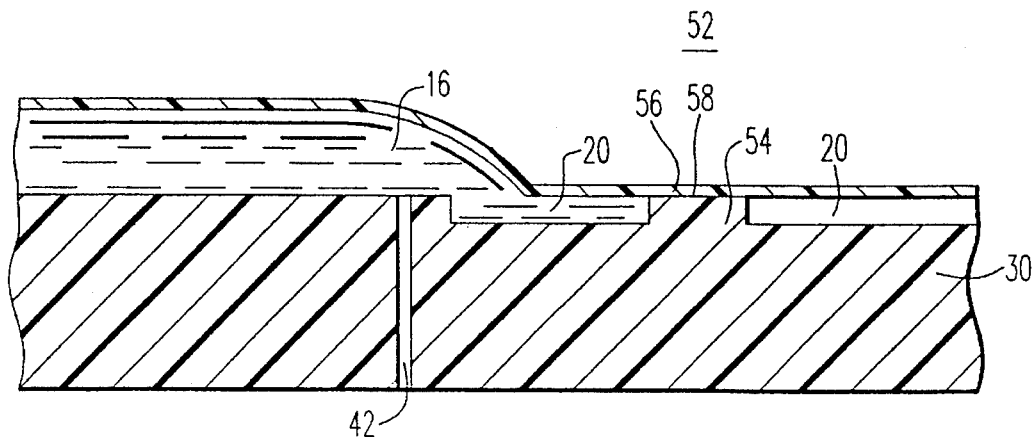
FIG. 3 is a cross-sectional view taken essentially along the line 3—3 of FIG. 2 showing a storage reservoir, controlling track, barrier and yielding member prior to actuation.
Figure 4:
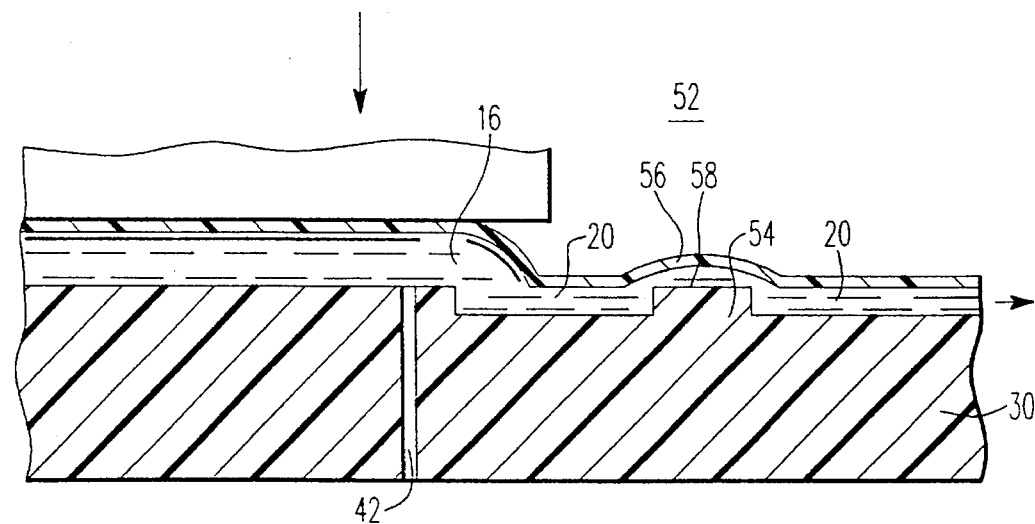
FIG. 4 is a view as in FIG. 3 illustrating a storage reservoir, controlling track, barrier and yielding member during actuation.

A means 52 for preventing the reagents from leaking from the reservoirs 16 due to jarring or dropping the device 10 is shown in FIGS. 1 and 2 and illustrated in cross-sectional view in FIGS. 3 and 4. The preferred means 52 for preventing reagent leaking until actuated by an operator utilizes a controlling track barrier 54 and a yielding member 56.

The barrier 54 is molded directly into the card 30 as shown in FIGS. 1–4. The barrier 54 is essentially a break in the controlling track 20 leading out of each reservoir 16. The top 58 of the barrier 54 is coplanar with the opposing surface 34 of the card 30. The wall of the barrier 54 closest to the reagents is preferably perpendicular to the bottom of the track 18 or has a reverse slope so that the fluid is not directed up over the barrier 54. A platen, which is used to seal the polyester film to the card 30, contains a cavity directly above the barrier 54. The cavity covers a larger area than the top 58 of the barrier 54. This cavity is vented to the ambient atmosphere, so that the heated air in the cavity can escape during sealing. If the cavity were not vented, the air within the cavity would increase in pressure, thereby causing the film to seal to the top 58 of the barrier 54. When the heat sealing operation is completed, the heat seal film ends up lying against the top 58 of the barrier 54, thus closing off the passage to the controlling track 20. This prevents the reagents from moving down the track 18 if the card 30 is jarred, shaken or dropped. However, when pressure is applied to the reagents contained in the reservoirs 16, such as occurs during actuation, the reagents will flow through the track 18 and over the top 58 of the barrier 54 by deflecting the yielding member 56, as illustrated in FIGS. 3 and 4.

The introduction of the barrier 54 into the track 18 also creates some resistance to the reagent flow when the reagents are forced out of the reservoirs 16. Some of the energy applied to the reservoirs 16 during actuation is used to push the fluid up and over the barrier 54. A portion of the energy is used to deform the yielding member 56.

The device 10 is intended for use with any reagents capable of utilization in determining the identity of a target analyte where the ease, convenience and reliability of having a self contained system are desired. Specifically, in an agglutination reaction, it is known in the art that a reaction between reagents and a target analyte may be designed to produce agglutination or the inhibition of agglutination.

However, a preferred embodiment of the present invention would utilize a latex agglutination reaction method for detection where antibodies are able to recognize minute quantities of the substance of interest, for example, cocaine. Latex agglutination reagents which detect various drugs of abuse are commercially available from Roche Diagnostics, Nutley, N.J.

Each of the known test kits is packaged as a set of three reagents for testing for cocaine, one of which is a solution of latex particles. For optimal effectiveness, the latex particle solution must be shaken immediately prior to use. This is recommended because the latex particles have a density greater than the surrounding solution causing the latex to settle over short periods of time.

It is preferred that the reagents used in the assay device 10 of the present invention eliminate the need for shaking the latex particle solution. The density of the latex particle solution is increased to equal the density of the latex particles thereby preventing particle settling.

Roche Diagnostics provides a latex agglutination test kit for cocaine detection containing: an antibody reagent A—one vial of mouse monoclonal anti-cocaine antibody in a buffered solution; reaction buffer B—one vial of buffer reagent; and latex reagent C—one vial of latex-cocaine particles in a buffered solution.

The Roche Diagnostics test requires the sequential addition of one drop of each reagent with an external or suspect sample. However, the procedure recommends "invert(ing) reagent C approximately 8 to 10 times before use. If excessive foaming is observed allow it to settle before using."

A preferred embodiment of the latex reagent would include the addition of 133 milligrams of sucrose in a final volume of 1 milliliter of latex reagent C creating a latex particle solution having a solution density of 1.05 gram/milliliter, equaling the density of latex particles. As a result, the latex particles remain suspended in the buffered solution and the requirement for inversion of reagent C prior to use is eliminated.

To assess the effectiveness, samples were tested utilizing the reformulated C reagent in the latex agglutination test for cocaine. Ten positive samples (buffer containing 100 parts per million cocaine) and ten negative samples (buffer containing 10 parts per billion cocaine (less than the cut-off value) were tested. Each test produced the appropriate positive or negative result.

This process can be used to enhance the effectiveness of other latex agglutination tests for drug detection. For instance, latex agglutination tests for morphine (heroin), phencyclidine (PCP), marijuana and methamphetamine are commercially available in a similar design as the cocaine test kit discussed above. Respective C reagents from each of these latex agglutination tests can be modified as described above resulting in an easier to use product.

In a preferred embodiment of the assay device 10 having three storage reservoirs 16 for containing the cocaine detecting reagents discussed above, the nozzles 28 at the head-on collision are not symmetrical. The nozzle 28 for the center reservoir 16 is only tapered in one dimension, instead of two. The point at which the collision occurs is not on the centerline of the downstream portion (20c or 20c') of the controlling track 20. The intersection is biased towards the center reservoir 16 so that more of the outer reservoir 16 reagent flows through the intersection. This is done because each of the three reservoirs 16 contain the same amount of reagent, but the contents of the center reservoir 16 is divided equally between the two initial collisions, i.e. one collision with the reagents of the other two reservoirs 16.

Figure 5:
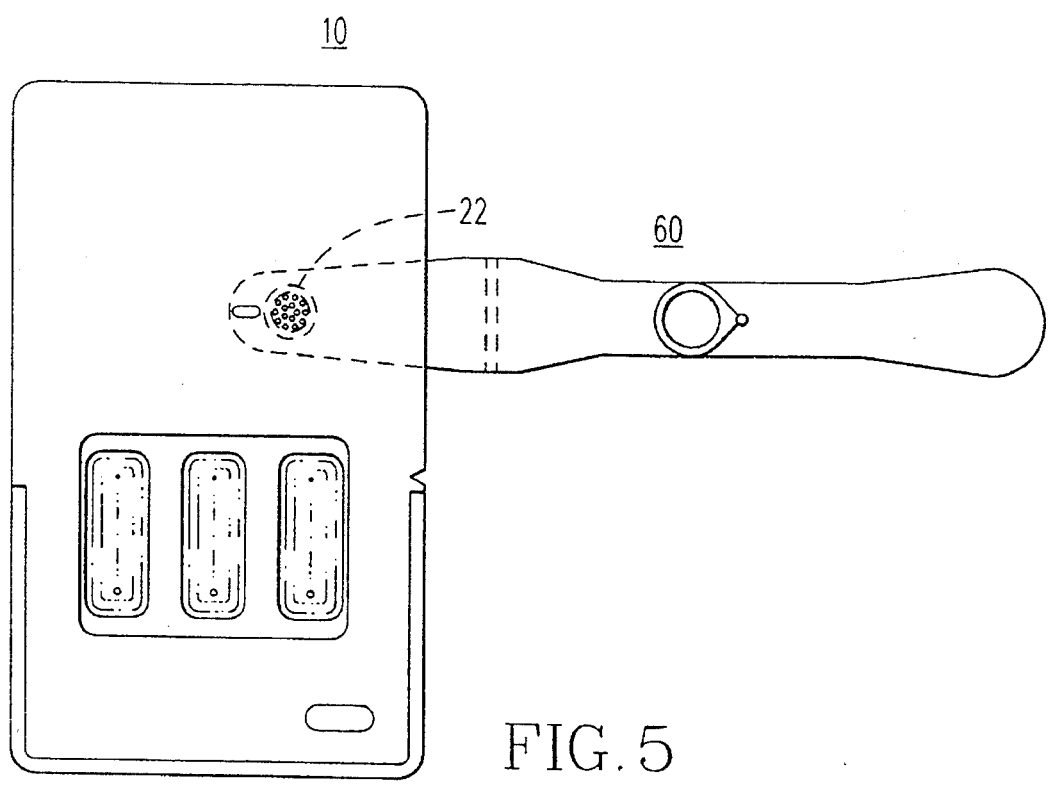
FIG. 5 is a top view of the preferred assay device with an engaged swab.

The shape of the nozzles 28, as well as the location of the collision point, work together to mix equal volumes of the reagent from the center reservoir 16 with the reagents from the remaining two reservoirs 16. The shape and size of the nozzle 28, along with the dimensions of the controlling track 20 preceding the nozzle 28, i.e., the cross-sectional areas of respective portion 20b, 20b' and 20b", can be adjusted based on the properties of the fluids involved and the mixing ratios desired A delivery means 60 for delivering the sample suspected of containing a target analyte into the device 10 is illustrated in FIG. 5. A preferred embodiment of the delivery means 60 for conveying the sample to the assay device 10 is a swab 60. FIG. 5 shows a top view of a preferred assay device 10 with the swab 60 engaged into the entry port 22. Swab 60 is used to collect an unknown sample by rubbing it in the sample or by simply moving it along a surface which is suspected of having been contaminated. The device 10 works by mixing the reagents contained in reservoirs 16 with the sample introduced to the system by the swab 60. After mixing, the results may be determined by analyzing the solution in the reacting track 24.

The cylindrical interface between the preferred swab 60 and the entry port 22 is both easy to manufacture(i.e. mold) and easy to use. A sharp, tapered ridge around the inside of the entry port 22 acts like the barb on a fishhook, allowing the swab 60 to be easily pushed past the ridge in one direction, while preventing it from easily being removed in the opposite direction. The ridge digs into the surface of the swab 60, which is preferably made of a soft plastic, to create a fluid seal.

The swab 60 illustrated in FIG. 6 is in the fully opened position, while FIG. 7 illustrates the closed or protected position. To improve the reliability of mixing the reagents with the sample, the gathering surface 62 of the swab 60 is covered with many closely spaced, small cones 64 which are used to collect the sample particles as the swab 60 is brushed across a surface. The cones 64 are preferably close to one another to grasp and hold the sample particles, while not being unnecessarily tall, minimizing the chance of forming bubbles and limiting the reagents needed to fill the entry port 22. A snap 66 on the swab 60 maintains the closed position until the user unfolds it for use. The design of the swab 60 enables the user to hold and open the swab 60 with one hand. The swab 60 is held in one hand with the middle of the fore finger behind a protective closure 68 and the thumb against a hinge 70 which creates a couple to snap the swab 60 open.

A preferred device 10 will minimize the bubbles created during actuation. Differences in height and the shape of the track 18 at various stages, as well as the cones 64 of the swab 60, tend to create air bubbles in the mixture which increases the difficulty in determining test results. Air bubbles can be a problem if caught in the track 18 under the optical viewing area 38, thus inhibiting the true reagent/analyte reaction from being observed.

A preferred entry port 22 is cylindrical to enhance fluid flow while minimizing bubble formation. The reagents are simultaneously injected, tangentially, into the entry port 22 such that the reagents collide once again before flowing past the cones 64, mixing with the sample particles as the reagents advance toward the reacting track 24. Since the controlling track 20 and the reacting track 24, where they are connected to the entry port 22, are both shallower than the entry port 22 to minimize the amount of required reagents, the track 18 is ramped into and out of the entry port 22. The reagents exit the entry port 22 and enter the reacting track 24 in a direction opposite to that which the reagents are injected into the entry port 22. This results in a more complete filling of the entry port 22 and better flushing of the samples from the collection cones 64.

An alternative embodiment of the swab 60 is illustrated in FIGS. 8 and 9 in the open and sealed position respectively. A hinge pin 72 is molded into the edge of the card 30 enabling the swab 60 to be snapped onto the card 30, thereby creating a device 10 with an attached hinged swab 60. The attached swab 60 incorporates a snap-on hinge 74 for attaching the swab 60 to the pin 72. Additionally, a retainer strip 76 is used to hold the attached swab 60 in a stored position, while keeping the gathering surface 62 clean and sealing the reagents inside the device 10.

The retainer strip 76, shown in FIG. 9, provides a means of sealing the entry port 22, sealing the ventilation hole 44 and protecting the swab gathering surface 62 between manufacture and final use of the device 10. The entry port 22 should be sealed to prevent reagent evaporation and contamination. The cones 64 of the attached swab 60 should be kept free of contamination prior to use. A preferred retainer strip 76 is one piece which performs the desired functions in a simple, easy to use manner. Preferably a narrow, thin strip of polyester film or similar material provides the main structure for the retainer strip 76. Portions of both sides of this strip 76 are adhesive coated so that it will stick to the device 10 and swab 60. It is desirable not to have adhesive over the ventilation hole 44 and entry port 22 since the adhesive may outgas into the track 18 resulting in reagent contamination during storage. A soft rubber pad 78 is laminated to the side of the strip 76 which is opposite the entry port 22 opening. The cones 64 of the gathering surface 62 are pressed into the pad 78 to prevent contamination. The swab 60 is held against the pad 78 by bending the retainer strip 76 over the tip of the swab 60 and adhering it to the back of the swab 60. Additionally, a detent feature in the hinge 74 helps keep the swab 60 against the pad 78.

To use the device, the free-end of the retainer strip 76 will be pulled off of the swab 60. The swab 60 can then be opened to its other detent position. The retainer strip 76 is then peeled off of the device 10, thus opening the entry port 22 and ventilation hole 44. The suspect sample can then be sampled with the swab 60 and then folded into the entry port 22 before actuating the device 10.

While a preferred delivery means 60 has been discussed in some detail, many other delivery means are available for introducing the sample to the assay device 10, such as, a syringe, dropper, pipette or even the hand of the user.

A means 80 for actuating is used to macroscopically mix reagents with the sample, then microscopically mix the reagents and sample to allow reaction to occur. The device 10 is preferably utilized in conjunction with a multi-speed actuation mechanism 80 which actuates the device 10 by squeezing the reagents from the reservoirs, mixing the reagents together, and then mixing the reagents with the suspect sample. The reagent and sample mixture may then be analyzed to determine sample identity. To insure that the reagents mix properly with the suspect sample and the proper reaction occurs, the mixing needs to be controlled and predictable. Both macroscopic, large scale mixing of the reagents, and microscopic, molecular diffusion, mixing takes place. The mechanism 80 provides the force and speed profiles to produce the desired mixing conditions.

Figure 10:
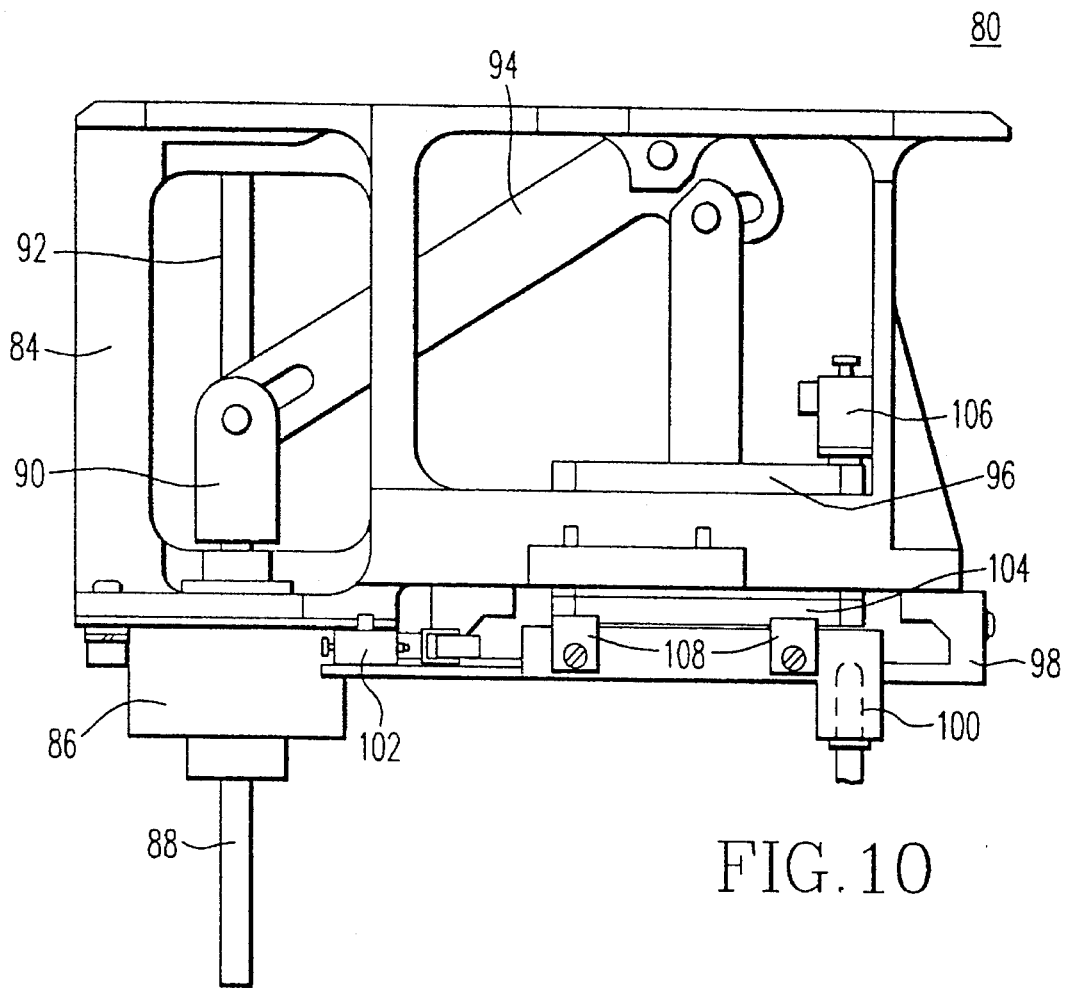
FIG. 10 is a side view of the preferred actuation mechanism.

FIG. 10 shows a side view of a preferred mechanism 80. The components shown includes a mechanism support 84, stepper motor 86, motor shaft 88, drive block 90, motor guide shaft 92, 10:1 mechanical advantage linkage 94, actuation block or platen 96, device or card guide 98, illuminating element such as an LED 100, on\off switch 102, and rubber pad 104. The device guide 98 is a separable subassembly from the actuation mechanism 80. The guide 98 is used to properly position the device 10 in the mechanism 80 by using keying features in the guide 98 and the device 10 to ensure proper device 10 orientation. The guide 98 houses the LED 100 used to illuminate the reaction product through the viewing area 38 and holds the mechanism on/off switch 102.

During operation, the motor shaft 88 moves 0.001 inch per motor pulse. The motor shaft 88 pushes on the drive block 90 which is guided by the motor guide shaft 92. This motion is translated to the linkage 94. The linkage 94 rotates clockwise about its pivot point. This rotary motion is transformed back to linear motion in the platen 96 by a pin in the platen 96 riding in a cam profile slot in the linkage 94. The platen 96 moves down 0.0001 inch when the motor shaft moves up 0.001 inch. The force output by the platen 96 is up to twenty-five (25) pounds which is ten (10) times the maximum motor force output of two and a half (2.5) pounds. The linkage 94 provides a ten (10) to one (1) mechanical advantage to the mechanism 80. The cam profile and straight slots in the linkage 94 maintain this relationship throughout the full range of mechanism 80 travel. The resulting motion of the platen 96 is one tenth ($\frac{1}{10}$) the motion of the motor shaft 92 with ten (10) times the output force of the motor 86. The amount of force generated by the mechanism 80 depends on the resistance to motion at the platen 96. If the mechanism 80 is operated without inserting a device 10, it will operate with no load. With the device 10 in place, the force transmitted to the platen 96 will equal the resistance from the reagents traveling in the track 18 and the amount of compression of the rubber pad 104 connected to the bottom of the platen 96.

A reset switch 106 is used to turn the motor 86 off when the mechanism 80 direction is reversed. This insures that the mechanism 80 will begin its motion profile from a known or home position. The rubber pad 104 is used to insure smooth actuation of the reservoirs 16. The pad 104 conforms to the reservoirs 16, resulting in equal or near equal actuation of each reservoir 16.

Detent springs 108 are used to hold the device 10 in position during actuation and provide positive device 10 insertion feedback to the user. When the device 10 is fully inserted, it snaps into place due to the force of the springs 108.

Figure 11:
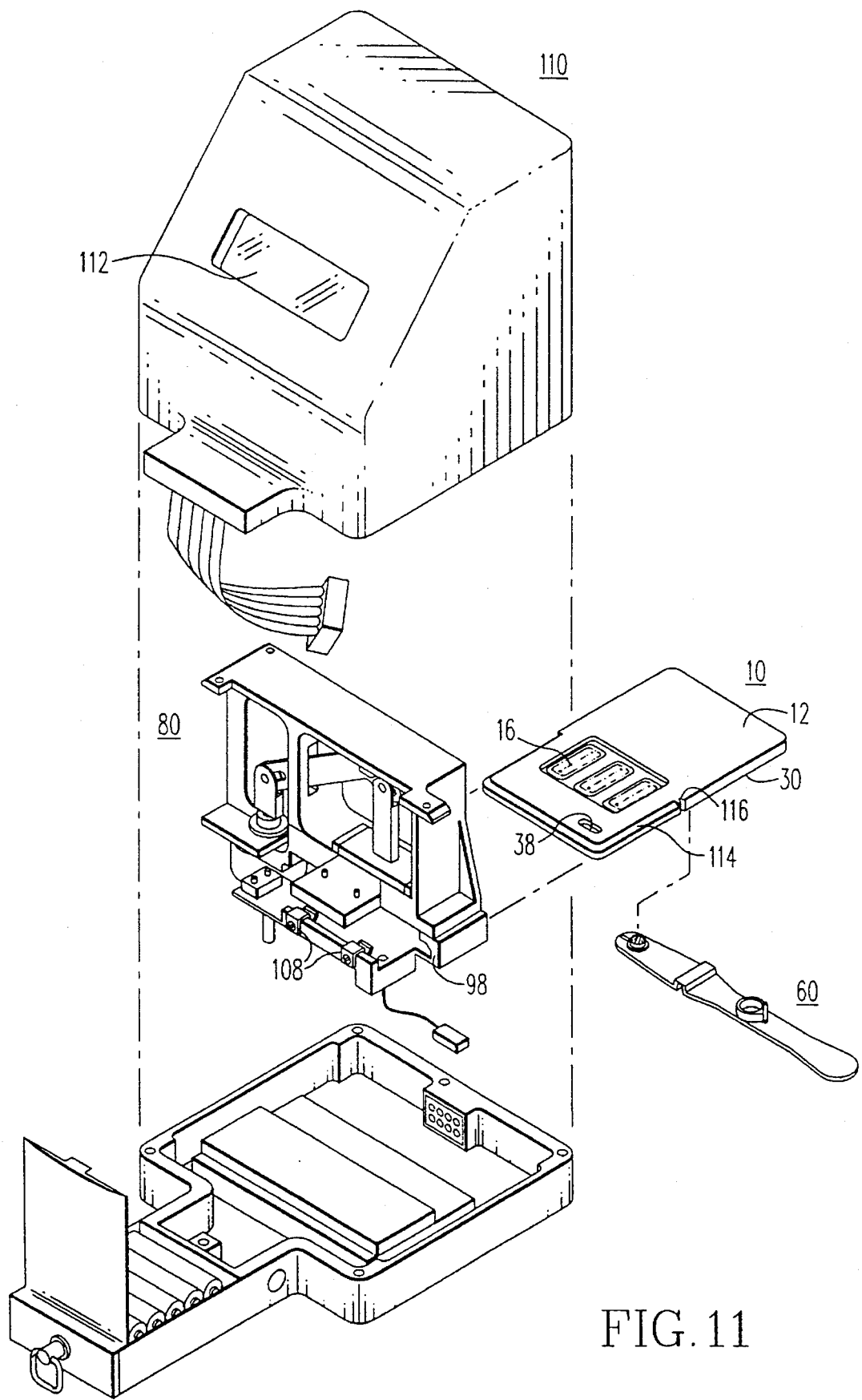
FIG. 11 is an exploded view of the assay device and swab in use with the actuator and electronics which evaluate the test results.

FIG. 11 shows an exploded view of a preferred hand held actuating and reading unit 110 including the actuation mechanism 80. The mechanism 80 provides the interface between the unit 110 and the assay device 10.

Once the sample is in the device 10, the device 10 is partially inserted into the unit 110. This action trips the switch 102 in the unit 110, causing its motor-driven platen 96 to squeeze the reservoirs 16, whereby the reagents flow into the track 18 to mix with each other and then the sample. Photoelectric detectors within an optics assembly view the resulting reaction product and transmit data to a processor. The processor analyzes the data, determines whether the sample does or does not contain the analyte of interest, and then sends the appropriate message to a display 112.

As shown in FIG. 11, one end of the cover member 12 of the assay device 10 has a chamfer 114 along the top edge and approximately half way up the adjacent sides. This is the end of the device 10 which is inserted into the unit 110. The end chamfer 114 provides a lead-in feature to assist in guiding the device 10 into a slot in the unit 110. The side chamfers 114 match up with corresponding features in the slot and guide 98. This prevents the device 10 from being inserted incorrectly, either upside-down or backwards.

When the device 10 is fully inserted into the unit 110, a V-shaped detent 116 in the edge of the card 30 and cover member 12 assembly accepts a spring-loaded ball when the device 10 is fully inserted. In addition to providing the user with tactile feedback, this detent 116 prevents the device 10 from falling out of the unit 110. When the device 10 is fully inserted into the unit 110, the on/off switch 102 is triggered, turning the unit 110 on. The motor 86 of the mechanism 80 actuates the linkage 94 and platen 96 that press on the reservoirs 16 of the device 10. The reagents are forced out of the reservoirs 16, mixed together in the controlling track 20, mix with the sample in the entry port 22, flow into the reacting track 24 and pass the viewing area 38. The mixing of the reagents which occurs in the controlling track 20 is macroscopic and is done with the mechanism 80 at a first speed creating a first flow rate. When the reagent and sample mixture flows pass the viewing area 38, the mechanism 80 is signaled to switch to a second speed creating a second flow rate less than the first flow rate for continued microscopic mixing of the reaction product.

In the preferred embodiment, the first speed is 200 motor pulses per second, while the second speed is 1 motor pulse every 1.6 seconds. The second speed is continued until the analysis of the reaction product passing the viewing area 38 is complete. Once the analysis is complete, the motor 86 direction is reversed, raising the platen 96 and pad 104 off the reservoirs 16 of the device 10. The unit 110 shuts off when the device 10 is removed.

The actuation mechanism 80 for use with an assay device 10 having a reservoir 16 containing reagent and a track 16 containing a sample connected to the reservoir 18 includes means for providing a first flow rate for mixing and delivering the reagent to the sample; and means for reducing the first flow rate to a second flow rate for further mixing the reagent and sample mixture to provide reaction time. This process can occur by applying pressure to the reservoirs 16 to force the reagent flow or by applying pressure directly to the reagent itself through a piston or plunger type arrangement. Although a preferred driving force is the stepper motor 86, other preferred driving forces are hydraulics, pneumatic or even using the air pressure itself to blow the reagent out of the reservoirs 16.

The actuation mechanism 80 also includes means for programming the means for providing the first flow rate and the means for reducing to the second flow rate according to the properties of the reagents and sample.

Finally, it has been determined that the second flow rate can occur by reversing the direction of the preferred actuation 80 to pull a vacuum, thereby causing the reagent and sample mixture flow to reverse direction. This can result in a smaller assay device 10 by minimizing the track 18 requirements. Using this preferred embodiment, the distinction between the controlling track 20 and the reacting track 24 is moot since a single length of track 18 serves both purposes.

Figure 12:
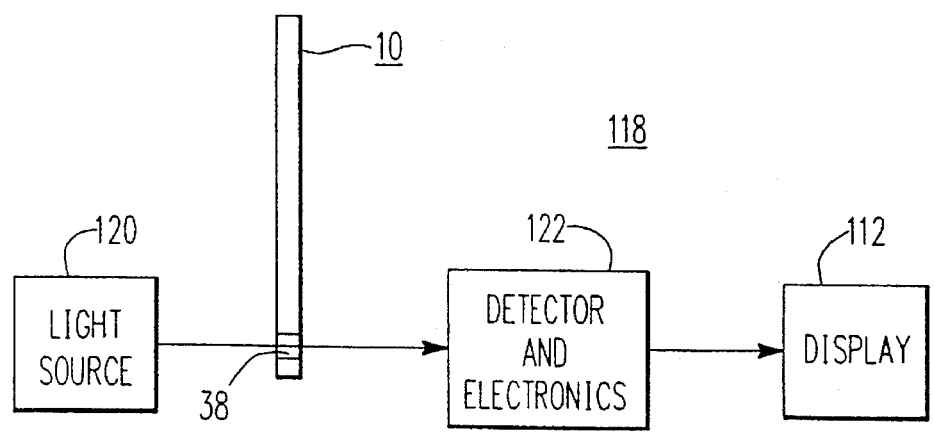
FIG. 12 is a schematic of the assay device in use with the electronics which evaluate the test results.

Observation of the optical view area 38 can be accomplished visually or can be automated by the use of electronic instrumentation depending on the type of detection chemistry utilized. This determination is preferably made utilizing an optics assembly 118 as schematically shown in FIG. 12.

The optics assembly 118 comprises an illuminating element or a transmitter 120 which projects light into the viewing area in a first direction and is transmitted through to an extent determined by the amount of agglutination which has occurred within the track 18 so that it impinges upon photodetectors or an optical receiver 122 where the amount of light transmitted can be measured. The results of this electronic determination is conveyed to the display 112. Thus, assembly 118 provides means for transmitting 120 light in a first direction toward the track 18 and means for detecting 122 the intensity of the light transmitted through the track 18.

Track 18 at the point of the viewing area 38 has a thickness which facilitates the use of small quantities of reagents, does not interfere with the agglutination process and is insufficient to substantially interfere with the passage of light through an aqueous reaction system contained therein. The thickness may be determined empirically and should simply be insufficient to interfere with the optical procedures. Moreover, since the reaction in accordance with the preferred embodiment of the present invention involves agglutination, track 18 must have sufficient thickness so that it does not mechanically interfere with the development and movement of the agglutinate.

The device 10 of the present invention may have great utility for detection of controlled drugs or materials such as explosives. In particular the device may be utilized to analyze for the presence of cocaine. A reaction environment is prepared in which the rate of an agglutination reaction is related in a smooth fashion to concentration over some useful range of a target analyte. A light source and photodetector monitor the reaction and measure the intensity of the light signal.

Although the present device 10 and system is based on the measurement of transmission through the track 18, it is also contemplated by and within the scope of the present invention that light reflectance from the track 18 might also be measured as an indicator of the extent of agglutination.

The method for determining the identity of an unknown sample comprises the steps of providing an assay device 10 as described above; introducing the sample into the device 10 by utilizing the means 60 for delivering the sample; forcing the reagents from the reservoirs 16 at a first flow rate through said controlling track 20 and into the entry port 22 containing the sample; and reducing the flow rate at which the reagents are forced out of the reservoirs 16 to a second flow rate so that the reagents and the sample mixture flows from the entry port 22 into the reacting track 24.

Another step in the method can include analyzing the result of the reagent and sample mixture. Analyzing the result includes transmitting light into the optical viewing area 38 in a first direction and detecting the intensity of light transmitted through the viewing area 38. Another method of determining the result of the test includes transmitting light into the viewing area 38 in a first direction and detecting the intensity of light reflected by the viewing area 38.

A method for actuating an assay card 10 having a reservoir 16 containing reagent and a track 18 containing a sample connected to said reservoir 16 comprises the steps of providing a first flow rate for mixing and delivering the reagent to the sample and reducing the first flow rate to a second flow rate for further mixing the reagent and sample mixture so that reaction can occur. Furthermore programming can be provided for varying the first and second flow rates according to the properties of the reagents and sample.

Determining the identity of an unknown sample employing an agglutination reaction wherein reagents are mixed and moved along a track 18, includes the improvement of forcing the reagents to move at a first flow rate for mixing the reagent with the sample and thereafter forcing the mixture to move at a second flow rate less than the first flow rate.

While there has been illustrated and described what are at present considered to be preferred embodiments of the present invention, it will be understood by those skilled in the art that various changes and modifications may be made, and equivalents may be substituted for elements thereof without departing from the true scope of the invention.

In addition, many modifications may be made to adapt a particular element, technique or implementation to the teaching of the present invention without departing from the central scope of the invention. Therefore, it is intended that this invention not be limited to the particular embodiments disclosed herein, but that the invention include all embodiments falling within the scope of the appended claims.

We claim:

1. An assay device for use in analyzing a sample of unknown substance by mixing assay reagents with the sample, comprising:
   (a) a housing having a plurality of storage reservoirs, each containing an assay reagent;
   (b) an entry port for receiving a sample suspected of containing a target analyte, into said housing, said entry port having an inlet and an outlet;
   (c) a controlling track for mixing and delivering the assay reagents in said reservoirs to said entry port via said inlet, and including a plurality of first portions each connected to a respective one of said reservoirs;
   (d) said controlling track including a plurality of second portions each for receiving assay reagent from a respective said first portion;
   (e) each said second portion including at least one discharge end in the form of a nozzle, said second portions being arranged that assay reagent discharging from a said nozzle of one of said second portions mixes with assay reagent discharging from a said nozzle of another of said second portions; and
   (f) means connected to said entry port to allow analysis of the mixed assay reagents and sample after passing through said entry port to said outlet.

2. An assay device as recited in claim 1 wherein:
   (a) each said second portion is adjacent another of said second portions and said discharge ends and therefore said nozzles of adjacent second portions face each other.

3. An assay device as recited in claim 2 wherein:
   (a) said controlling track further comprises at least a third portion which is substantially perpendicular to said facing nozzles so that the flow of assay reagents during mixing is diverted at approximately a ninety-degree angle after a head-on collision of said assay reagents when discharged from said nozzles.

4. An assay device as recited in claim 2 wherein:
   (a) the cross-sectional area of each said first portion is less than the cross-sectional area of the second portion to which it is connected.

5. An assay device as recited in claim 1 wherein:
   (a) said entry port is circular; and
   (b) said controlling track further comprises a final section having at least two branches each of which discharges the mixed assay reagents tangentially into said circular entry port.

6. An assay device as recited in claim 1 which further comprises:
   (a) means disposed relative to said reservoirs for discharging said assay reagents in said reservoirs into said controlling track by applying pressure to said storage reservoirs.

7. An assay device as recited in claim 6 wherein:
   (a) said means for discharging initially discharges said assay reagents at a first flow rate and thereafter at a second and slower flow rate.

8. An assay device as recited in claim 6 which further comprises:
   (a) means for preventing said assay reagents from leaking out of said storage reservoirs into said controlling track until said means for discharging is activated.

9. An assay device as recited in claim 7 wherein:
   (a) said means for discharging applies a first pressure to said reservoirs to produce said first flow rate and a second and lower pressure to produce said second flow rate.

10. An assay device as recited in claim 8 wherein:
    (a) said means for preventing comprises:
        (i) a barrier in each said first section of said controlling track; and
        (ii) a yielding member normally contacting said barrier, said yielding member moving in response to pressure from said assay reagent when said means for discharging is activated.

11. An assay device as recited in claim 1 wherein the means connected to the entry port comprises:
    (a) a reacting track fluidly connected to said entry port for reacting said assay reagents and said sample;
    (b) said reacting track having an optical viewing area for viewing reaction results of mixing the reagents and said sample.

12. An assay device as recited in claim 11 which further comprises:
    (a) an accumulator reservoir in said reacting track for retaining excess assay reagent and sample mixture.

13. An assay device as recited in claim 11 which further comprises:

(a) means, positioned relative to said optical viewing area, for detecting said reaction results.

14. An assay device as recited in claim 13 wherein:
(a) said means for detecting comprises:
  (i) light transmitting means operable to project light into said optical viewing area, and
(b) An optical receiver positioned for determining the amount of light transmitted through said optical viewing area.

15. An assay device as recited in claim 13 wherein:
(a) said means for detecting comprises:
  (i) light transmitting means operable to project light into said optical viewing area, and
  (ii) an optical receiver positioned for determining the amount of light reflected from said optical viewing area.

16. An assay device as recited in claim 1 which further comprises:
(a) means for delivering said sample to said entry port.

17. An assay device as recited in claim 16 wherein:
(a) said means for delivering comprises a swab for collecting said sample;
(b) said swab having a plurality of projections thereon for contacting said sample.

18. An assay device as recited in claim 17 wherein:
(a) said swab is attached to said assay device.

19. An assay device as recited in claim 1 wherein:
(a) said housing has three storage reservoirs containing assay reagents for utilization in detecting cocaine.

20. An assay device as recited in claim 19 wherein:
(a) said assay reagents in said storage reservoirs consist of:
  (i) an antibody reagent of mouse monoclonal anti-cocaine antibody in a buffered solution, in one of said reservoirs;
  (ii) a reaction buffer reagent in another one of said reservoirs; and in the third of said reservoirs,
  (iii) a latex reagent of latex-cocaine particles in a buffered solution, said latex regent having sucrose added for increasing the density of said latex reagent to approximately equal to the density of said latex particles.

* * * * *